United States Patent [19]
Rhubright

[11] Patent Number: 5,811,580
[45] Date of Patent: Sep. 22, 1998

[54] PROCESS FOR THE PREPARATION OF N-HYDROCARBYL-SUBSTITUTED AMIDES VIA THE RITTER REACTION USING SOLID CLAY CATALYSTS

[75] Inventor: Douglas C. Rhubright, Chardon, Ohio

[73] Assignee: The Lubrizol Corporation, Wickliffe, Ohio

[21] Appl. No.: 760,077

[22] Filed: Dec. 4, 1996

[51] Int. Cl.$^6$ .................................................. C07C 231/06
[52] U.S. Cl. .......................... 564/128; 564/126; 564/129; 564/130; 564/131
[58] Field of Search .................... 564/126, 128, 564/129, 130, 131

[56] References Cited

U.S. PATENT DOCUMENTS

| | | | |
|---|---|---|---|
| 3,151,157 | 9/1964 | Fugate et al. | 260/561 |
| 4,273,938 | 6/1981 | Merger et al. | 564/124 |
| 5,107,027 | 4/1992 | Knifton et al. | 564/485 |
| 5,304,681 | 4/1994 | Knifton et al. | 564/485 |
| 5,334,775 | 8/1994 | Guiterrez et al. | 568/780 |
| 5,366,945 | 11/1994 | Kresge et al. | 502/60 |
| 5,387,715 | 2/1995 | Karasawa et al. | 564/124 |

FOREIGN PATENT DOCUMENTS 3-93765   9/1989   Japan .......................... C07C 271/06

OTHER PUBLICATIONS

H. Plaut and J.J. Ritter, A New Reaction of Nitriles, VI. Unsaturated Amides *J. Am. Chem. Soc.*, vol. 73 (1951) pp. 4076–4077.

Olah et al., Nafion–H® Catalyzed Beryer–Villiger Oxidation and Ritter Reactions, *Materials Chemistry and Physics*, vol. 17 (1987), pp. 21–30.

Alkylation of Diphenylamine with α–Methlstyrene and Diisobutylene Using Acid–Treated Clay Catalysts," Chitnis et al., *Journal of Catalysis*, 160, 84–94, (Jun., 1996).

*Primary Examiner*—Shailendra Kumar
*Attorney, Agent, or Firm*—Krishna G. Banerjee; David M. Shold

[57] ABSTRACT

Hydrocarbyl-substituted amides can be prepared in a catalyzed Ritter reaction by contacting a nitrile with a hydrocarbylating agent, in the presence of an acidified clay as the catalyst, under conditions conducive to the formation of the hydrocarbyl-substituted amide.

37 Claims, No Drawings

PROCESS FOR THE PREPARATION OF N-HYDROCARBYL-SUBSTITUTED AMIDES VIA THE RITTER REACTION USING SOLID CLAY CATALYSTS

BACKGROUND OF THE INVENTION

The present invention relates to an improved process for the preparation of N-hydrocarbyl-substituted amides.

It is known to react secondary and tertiary alcohols, olefins and water, or esters with nitriles in the presence of acids, such as sulfuric acid, to give N-alkyl-substituted amides. This reaction is known as the Ritter reaction. H. Plaut and J. J. Ritter, A New Reaction of Nitriles. VI. Unsaturated Amides, J. Am. Chem. Soc., vol. 73 (1951), pp. 4076–4077, discloses the reaction of nitriles with olefins or alcohols to yield N-substituted amides, in particular, unsaturated amides.

U.S. Pat. No. 3,151,157, Fugate et al., Sep. 29, 1964, discloses the preparation of N-alkylacrylamide by reacting a straight chain olefin and acrylonitrile in the presence of strong sulfuric acid in a preformed reaction product of said olefin, acrylonitrile and strong sulfuric acid.

It is known to promote Ritter reactions with organic cation exchangers, such as Nafion-H®, a perfluorinated sulfonic acid resin. U.S. Pat. No. 4,273,938, Merger et al., Jun. 16, 1981 discloses the preparation of N-substituted carboxylic acid amides by reacting cyano compounds, e.g., acrylonitrile, with olefins and water in the presence of organic cation exchangers containing sulfonic acid groups.

Olah et al., Nafion-H® Catalyzed Baeyer-Villiger Oxidation and Ritter Reactions, Materials Chemistry and Physics, vol. 17 (1987), pp. 21–30, discloses the use of Nafion-H® to promote the reaction of alcohols in the presence of nitriles to yield amido compounds.

"Alkylation of Diphenylamine with α-Methylstyrene and Diisobutylene Using Acid-Treated Clay Catalysts," Chitnis et al., Journal of Catalysis, 160, 84–94 (June, 1996) discloses the use of acid-treated clays as catalysts on laboratory/industrial scales. The catalyst can be partially regenerated under certain conditions.

SUMMARY OF THE INVENTION

The present invention now provides a process for the preparation of a hydrocarbyl-substituted amide, comprising contacting:

(a) a nitrile with
(b) a hydrocarbylating agent, in the presence of
(c) a catalyst comprising an acidified clay under conditions conducive to the formation of the hydrocarbyl-substituted amide. The invention further provides the product prepared thereby.

DETAILED DESCRIPTION OF THE INVENTION

The present invention provides a process for the preparation of an N-hydrocarbyl-substituted amide, comprising contacting a nitrile with a hydrocarbylating agent in the presence of a catalyst comprising an acidified clay under conditions conducive to the formation of the hydrocarbyl-substituted amide. The invention further provides the product prepared thereby.

The process according to the invention in the case where an alcohol is employed as the hydrocarbylating agent is represented as shown:

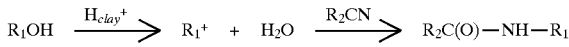

wherein $R_1$ and $R_2$ denote hydrocarbyl, $R_1^+$ denotes a carbonium ion, and $H_{clay}^+$ denotes a clay species. The process according to the invention in the case where an olefin is employed as the hydrocarbylating agent is represented as shown:

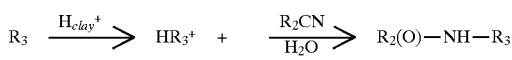

wherein $R_3$ denotes an olefin or substituted olefin, $HR_3^+$ denotes the carbonium ion formed by the operation of an acidified clay upon the olefin, and $HR_3$ represents the hydrocarbyl group derived from the olefin. In the case where an olefin is employed as the hydrocarbylating agent, contacting at least one mole of water per mole of olefin with the olefin $R_3$, the nitrile $R_2$, in the presence of the acidified clay, $H_{clay}^+$, is conducive to the formation of the N-hydrocarbyl-substituted amide product.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy and phosphorus-containing substituents);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

REAGENT ONE: NITRILE

Nitriles are a diverse category of compounds which are characterized by a cyano group, —CN, directly attached to the remainder of the molecule. As will be illustrated below, a wide variety of nitriles can be used in the Ritter reaction. The nitriles of the present invention have the formula $R_2CN$, where $R_2$ denotes hydrogen, a hydrocarbyl, or a second cyano group. The hydrocarbyl $R_2$ groups of the nitriles will usually comprise hydrocarbon substituents, but can also comprise substituted hydrocarbon substituents and hetero substituents.

The hydrocarbon substituent $R_2$ groups will usually include aliphatic, e.g., alkyl or alkenyl groups, but can also include aromatic groups; and aliphatic- or aromatic-substituted aromatic groups.

The substituted hydrocarbon substituent $R_2$ groups of the nitriles of the present invention will usually include aliphatic, aromatic, and aliphatic- or aromatic-substituted aromatic groups which can be substituted with such non-hydrocarbon groups as halo—for example chloro and fluoro; hydroxy; alkoxy; nitro; amino; and alkyl-substituted amino.

The hetero substituent $R_2$ groups of the nitrites contain heteroatoms such as nitrogen and oxygen.

For purposes of the present invention, the preferred nitrites are aliphatic nitrites. The nitriles can be saturated, or preferably, unsaturated. In one embodiment, the $R_2$ group of the nitrile is an alkenyl group, more preferably a vinyl group. In another embodiment, the $R_2$ group of the nitrile is an alkyl group, preferably a propyl group.

Typical Nitriles Useful in the Present Invention

A typical aliphatic nitrile moiety useful in the present invention having an alkenyl hydrocarbon substituent $R_2$ group is acrylonitrile. A typical aliphatic nitrile moiety useful in the present invention and having an alkyl hydrocarbon substituent $R_2$ group is butyronitrile. For such reasons as cost, availability, performance, and similar considerations, the $R_2$ group of the nitrile of the present invention is normally an alkenyl nucleus or an alkyl nucleus. Most preferably the $R_2$ group is a vinyl group. Thus, the most preferred nitrile of the present invention is acrylonitrile. In another embodiment, the nitrile can be a saturated nitrile, such as butyronitrile.

Illustrative Nitriles Useful in the Present Invention

A wide variety of other materials can serve a function similar to the typical nitriles of the present invention. Such materials include aliphatic nitriles having alkyl or alkenyl hydrocarbon substituent $R_2$ groups, cyclic nitriles having aromatic-, aliphatic-, or non-hydrocarbon-substituted $R_2$ groups, aliphatic nitriles having substituted hydrocarbon substituent $R_2$ groups, nitriles having hetero-substituted substituent $R_2$ groups, and dinitriles.

Illustrative aliphatic nitrile moieties useful in the present invention and having alkyl hydrocarbon substituent $R_2$ groups are represented as shown:

$CH_3C\equiv N, CH_3CH_2C\equiv N, CH_3(CH_2)_nC\equiv N$, where n=1–16.

Illustrative aliphatic nitrile moieties useful in the present invention and having alkenyl hydrocarbon substituent $R_2$ groups are represented as shown:

$CH_2CHCN, CH_2C(CH_3)CN$.

Illustrative cyclic nitrile moieties of the present invention having aromatic-, aliphatic-, or non-hydrocarbon-substituted $R_2$ groups are represented graphically as shown:

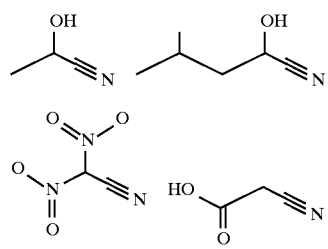

Illustrative aliphatic nitrile moieties having substituted hydrocarbon substituent $R_2$ groups are represented graphically as shown:

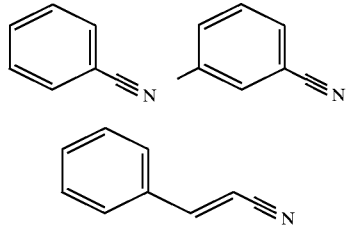

as well as amine-substituted and halogen substituted species.

Illustrative dinitrile moieties useful in the present invention are represented as shown:

$N\equiv CC\equiv N, N\equiv CCH_2C\equiv N, N\equiv CC_2H_4C\equiv N, N\equiv CC_3H_6C\equiv N$ and $N\equiv CC_4H_8C\equiv N$. Among these, adiponitrile is preferred.

REAGENT TWO: HYDROCARBYLATING AGENT

The nitrile is reacted with a hydrocarbylating agent under conditions conducive to the formation of the hydrocarbyl-substituted amide. The term "hydrocarbylating agent" is analogous to the conventional term "alkylating agent" except that it further encompasses hydrocarbyl groups as distinguished from solely alkyl groups. Hydrocarbyl groups are materials which may have a relatively small number of heteroatoms or substituents which do not impede the reaction and do not alter the substantially aliphatic hydrocarbon nature of the group, consistent with the commonly understood meaning of the term "hydrocarbyl."

A hydrocarbyl group evinces a substantially aliphatic hydrocarbon nature for the purposes of the present invention if it is susceptible to formation into a carbonium ion, represented as $R_5R_6R_7C+$, wherein $R_5$, $R_6$, and $R_7$ are independently hydrogen or hydrocarbyl. Preferably at least one of $R_5$, $R_6$, and $R_7$ is hydrocarbyl.

The preferred hydrocarbylating agents of the present invention are in fact alkylating agents. Alkylating agents are materials which react with another material, under appropriate conditions, typically acid catalyzed conditions, to add an (or an additional) alkyl group on the other material. Alkylating agents are well known materials and include alcohols and the reactive equivalents of alcohols. More specifically, alkylating agents include alcohols, olefins, esters, hydroxy esters, carboxylic acids, ketones, ethers, and alkyl halides.

For purposes of the present invention, the preferred hydrocarbylating agents are alcohols, more preferably mono-alcohols. The alcohols can be primary, secondary, or, preferably, tertiary. In one embodiment, the alcohol contains 2 to 24 carbon atoms, preferably 3 to 16, and more preferably 4 to 8 carbon atoms.

Typical Hydrocarbylating Agents Useful in the Present Invention

A typical tertiary mono-alcohol moiety useful as a hydrocarbylating agent in the present invention is tert-butyl alcohol. Other tertiary mono-alcohol moieties include 2,4,4-trimethyl-2-pentanol and 4-oxo-2-methylpentanol. A typical secondary mono-alcohol moiety is 2-propanol. A primary alcohol is 2,4,4-trimethyl-1-pentanol, which may rearrange during reaction to provide a tertiary cation. A typical olefinic-ally unsaturated anhydride moiety is 2-methyl-2-propenyl succinic anhydride. Typical α-olefin moieties include 2-methyl-1-propene, 2,4,4-trimethyl-1-pentene, and 1-propene. A typical β-olefin moiety useful as a hydrocarbylating agent in the present invention is 2,4,4-trimethyl-2-pentene. A typical halo-substituted olefin moiety is 1-chloro-isoprene. A typical di-olefin moiety is 1,3-butadiene. A typical non-hydrocarbon-substituted olefin moiety 1-carboxy-2-methyl propene. A typical ether moiety is the cyclic ether oxirane. A typical ketone moiety is acetone. An example of an alcohol hydrocarbylating agent is EMKROX® AF-20, a propoxylated $C_{14-16}$ alcohol, which has alkoxy structure in addition to alcohol functionality, and is represented as shown:

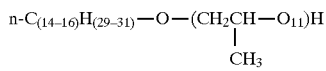

Related materials include other alkoxylated alcohols, including mixtures of alkoxylated alcohols such as ethoxylated, propoxylated, and butoxylated alcohols.

For such reasons as cost, availability, performance, and similar considerations, the hydrocarbylating agent of the present invention is normally an alcohol or a reactive equivalent thereof, such as an acetal. Preferably the alcohol is a mono-alcohol. Most preferably the hydrocarbylating agent is a tertiary mono-alcohol. Thus, the most preferred hydrocarbylating agent of the present invention is tert-butyl alcohol.

In another embodiment, the hydrocarbylating agent can be a tertiary mono-alcohol such as 2,4,4-trimethyl-2-pentanol or 4-oxo-2-methylpentanol. In yet another embodiment, the hydrocarbylating agent can be a secondary mono-alcohol such as 2-propanol. In a further embodiment, the hydrocarbylating agent can be an olefinically unsaturated anhydride such 2-methyl-2-propenyl succinic anhydride. In another embodiment, the hydrocarbylating agent can be an α-olefin such as 2-methyl-1-propene, 2,4,4-trimethyl-1-pentene, or 1-propene.

In yet another embodiment, the hydrocarbylating agent can be a β-olefin such as 2,4,4-trimethyl-2-pentene. In a further embodiment, the hydrocarbylating agent can be a halo-substituted olefin such as 1-chloro-isoprene. In another embodiment, the hydrocarbylating agent can be a di-olefin such as 1,3-Butadiene. In yet another embodiment, the hydrocarbylating agent can be a non-hydrocarbon-substituted olefin such as 1-carboxy-2-methyl propene. In a further embodiment, the hydrocarbylating agent can be a cyclic ether such as oxirane. In another embodiment, the hydrocarbylating agent can be a ketone such as acetone, $CH_3C(O)CH_3$ or its acetal form, such as $CH_3C(OCH_3)_2CH_3$. In yet another embodiment, the hydrocarbylating agent can be a non-hydrocarbon substituted moiety such as a propoxylated alcohol.

Illustrative Hydrocarbylating Agent Alcohols

A wide variety of materials can serve a function similar to the typical hydrocarbylating agent alcohols of the present invention. Such materials include various primary alcohols; aliphatic, alicyclic, and alicyclic-substituted secondary alcohols; aromatic-, aromatic- and alicyclic-, or halo- (e.g., chloro- or bromo-) substituted secondary alcohols; alkyl- and aromatic-substituted aliphatic tertiary alcohols; tertiary alcohols having both aromatic and alicyclic substituents, or cyclic substituents wherein the ring is completed through another portion of the molecule (e.g., two substituents together form an alicyclic radical); tertiary alcohols having an olefinic bond; amido-, amino-, nitro-, carboxy-, halo- (e.g., fluoro- and/or chloro-), alkoxy-substituted tertiary alcohols; and hetero-substituted tertiary alcohols.

Illustrative primary alcohols useful as hydrocarbylating agent moieties in the present invention include ethanol, propanol, linear and branched 1-alkanols having 4 to 24 carbon atoms, cyclohexylmethanol, benzyl alcohol, and substituted benzyl alcohols (methyl, dimethyl, methoxy, etc.)

Illustrative aliphatic, alicyclic, and alicyclic-substituted secondary alcohols useful as hydrocarbylating agent moieties in the present invention include 2-propanol, 2-butanol, 2-pentanol, 3-pentanol, 2-hexanol, 2-heptanol, 2-ethylhexanol, cyclopentanol, cyclohexanol, and 1-cyclohexylethanol.

Illustrative aromatic-, aromatic- and alicyclic-, or halo- (e.g., chloro- or bromo-) substituted secondary alcohols useful as hydrocarbylating agent moieties in the present invention include α-methylbenzyl alcohol, α-ethylbenzyl alcohol, α-chloroethylbenzyl alcohol, α-sec-propylbenzylalcohol, α-cyclohexyl-benzyl alcohol, cumyl alcohol (2-phenylisopropanol), dicumylalcohol (α,α,α',α'-tetramethylbenzenedimethanol) and benzhydrol.

Illustrative alkyl- and aromatic-substituted aliphatic tertiary alcohols useful as hydrocarbylating agent moieties in the present invention include t-butanol, t-pentanol, 3-methyl-3-hexanol, and α,α-dimethylbenzyl alcohol.

Illustrative tertiary alcohols having both aromatic and alicyclic substituents, or cyclic substituents wherein the ring is completed through another portion of the molecule (e.g., two substituents together form an alicyclic radical) useful as hydrocarbylating agent moieties in the present invention include 1-methylcyclohexanol, 1-phenylcyclohexanol, and 1-adamantanol.

Illustrative tertiary alcohols having an olefinic bond and useful as hydrocarbylating agent moieties in the present invention include 3-methylhex-1-ene-3-ol and 3-methyl-1-phenylhept-1-ene-3-ol.

The hydrocarbylating agent moieties can also include amido-, amino-, nitro-, carboxy-, halo- (e.g., fluoro- and/or chloro-), and alkoxy-substituted tertiary alcohols, and hetero-substituted tertiary alcohols.

Glycols can also function as hydrocarbylating agents.

Illustrative Hydrocarbylating Agent Olefins

A wide variety of materials can serve a function similar to the typical hydrocarbylating agent olefins of the present invention. Such materials include various aliphatic and alicyclic-substituted α-olefins; aryl-substituted α-olefins; aliphatic , β-olefins; aryl-substituted β-olefins; hetero-substituted , β-olefins; cyclic olefins; and di-olefins.

Illustrative aliphatic and alicyclic-substituted α-olefins useful as hydrocarbylating agent moieties in the present invention ethylene, propylene, butylene, and other linear and branched α-olefins including 2-methylpropene, 2-methyl-1-butene, and 2-methyl-3-chloropropene.

Illustrative aryl-substituted α-olefins useful as hydrocarbylating agent moieties in the present invention include styrene and the various ring- and α-substituted styrenes, and homologues such as 3-phenyl-1-propene.

Illustrative aliphatic β-olefins useful as hydrocarbylating agent moieties in the present invention include 2-butene, 3-methyl-2-butene, and 2-methyl-2-pentene. Illustrative aryl-substituted , β-olefins include phenylpropene and substituted versions thereof.

Illustrative cyclic olefins useful as hydrocarbylating agent moieties in the present invention include cyclohexene and substituted cyclohexenes.

Illustrative di-olefins useful as hydrocarbylating agent moieties in the present invention include 1,4-butadiene, 2,5-hexadiene, divinylbenzene, di(1-methylvinyl)benzene, dicyclopentadiene, and tricyclohepta-2,5-diene.

Other Illustrative Hydrocarbylating Agents

A wide variety of materials can serve a function similar to the typical hydrocarbylating agent olefins, alcohols, anhydrides, ketones, and ethers of the present invention. Such materials include various esters; carboxylic acids; glycols; ethers; alkyl halides; aldehydes; and ketones.

Illustrative carboxylic acids include acetic acid, propionic acid, butyric acid, other alkanoic acids, trimethylacetic acid, stearic acid, and oleic acid.

Illustrative esters include the esters of each of the foregoing carboxylic acids, including methyl acetate, ethyl acetate, and other alkyl alkanoates.

Illustrative glycols include ethylene glycol, 1,2-propylene glycol, and glycerol.

Illustrative ethers include diethyl ether, methyl propyl ether, dipropyl ether, and methyl butyl ethers such as methyl-t-butyl ether, as well as diethers and polyethers.

Alkyl halides include, preferably, t-butyl chloride.

Aldehydes and ketones can also function as hydrocarbylating agents for purposes of the present invention. Illustrative aldehydes include formaldehyde, acetaldehyde, propionaldehyde, pentanaldehyde, benzaldehyde, and cyclohexanaldehyde. Illustrative ketones include acetone, butanone, cyclohexanone, methyl ethyl ketone, acetophenone, and substituted versions thereof.

For such reasons as cost, availability, performance, and similar considerations, the hydrocarbylating agent of the present invention is normally a mono-alcohol. Most preferably the hydrocarbylating agent is a tertiary mono-alcohol. Thus, the most preferred hydrocarbylating agent of the present invention is tert-butyl alcohol.

CATALYST: CLAY

Reactions of a nitrile and a hydrocarbylating agent to form an N-hydrocarbyl-substituted amide are generally acid-promoted reactions. The term "acid-promoted" instead of "acid-catalyzed" is used to describe the action of an acid in the context of a conventional Ritter reaction because the acid employed therein, usually sulfuric acid, is consumed in the reaction or during the subsequent workup, generating at least one mole of sulfate waste per mole of product.

In contrast to sulfuric acid, the ideal catalyst remains substantially unaltered by the reaction in which it participates. The clays employed for the amide synthesis reactions of the present invention retain catalytic activity over the course of several Ritter reactions, thus evincing the sustained catalytic activity properties of the ideal catalyst. These properties are markedly absent in the acids used to promote conventional Ritter reactions. Thus the term "acid-promoted" rather than "acid-catalyzed" is used to describe the action of ordinary acids in the reaction of a nitrile and a hydrocarbylating agent to form an N-hydrocarbyl-substituted amide.

In addition, sulfuric acid-promoted Ritter reactions generate at least one mole of sulfate waste per mole of product. The sulfate waste must then be disposed of in accordance with applicable environmental regulations, often at considerable cost. In contrast, the solid acidic clays employed for the amide synthesis reactions of the present invention exhibit catalytic activity over the course of several Ritter reactions and do not generate aqueous sulfate waste. Moreover, the product can be separated from the solid reactants and the clay without quenching, neutralization, or water washing. Thus the system is amenable to operation under continuous stirred tank reaction or plug flow reaction conditions, in which catalyst solids are retained in the reactor and liquid products are removed.

The catalyst for the process of the present invention is an acidified clay. Clays in general are naturally occurring layered silicates which are essentially crystalline materials of very fine particle size, generally less than 2 μm. Acidified clays can be prepared from those clays which contain exchangeable cations, which include those of the smectite, vermiculite, mica, and brittle mica groups. Typical clays in these groups include montmorillonite, hectorite, saponite, laponite, beidellite, vermiculite (dioctahedral and trioctahedral), muscovite, phlogopite, taeniolite, margarite, and clintonite.

Clays can be acidified by treatment with an acid, i.e., a source of $H^+$ ions. Typically the clay will be acidified to a level of 0.1 to 1.0 mole $H^{3O}$ per g of clay. Acidification can be effected by treatment of the clay with any of a variety of acids, e.g., either a Lewis acid or a Brønsted acid, and organic or inorganic acids. Particularly suitable acids include sulfuric acid and phosphoric acid. The extent of treatment with acid will typically provide 0.1 to 1.0 equivalents of acid per gram of clay. Superfiltrol™ is an example of an acidified clay of the montmorillonite type, available from Englehard with a typical acidity of 5 mg KOH/g (0.2805 mole $H^+$/g catalyst). Another example is F-24, also an acidified montmorillonite clay from Engelhard, having a residual acidity of 16 mg KOH/g and a surface area (BET method) of 350 $m^2$/g. The mechanism of the acid site generation, as well as a description of certain reactions catalyzed by such materials, is described, for instance, in Y. Izumi et al., "Zeolite, Clay, and Heteropolyacid in Organic Reactions," VCH Publishers, 1992, page 74 et seq. Descriptions of various types of clays, as mentioned above, is found in this same reference at pages 50–52.

THE METHOD

The actual process of hydrocarbylation of the nitrites can be either a continuous or batchwise process in which the nitrile, the hydrocarbylating agent and the catalyst are contacted for a suitable period of time, often at an elevated temperature. The components can be reacted neat, or an inert solvent can be employed, including hydrocarbon solvents such as hexane or cyclohexane. Often excess nitrile is employed as a portion of the reaction medium.

The reaction can also be conducted under conditions such that the nitrile and the alkylating agent are present in the gas phase; however, more commonly a liquid phase reaction is more convenient and is thus preferred. Thus the mixture of reagents and catalyst can be contacted generally from room temperature or above, up to a temperature determined largely by the onset of decomposition of the materials or, if a liquid phase reaction is desired, the boiling point of the lowest boiling component of the mixture. Typically, for a liquid phase reaction, the temperature will be 50° to 250° C., preferably 50° to 150° C., more preferably 60° or 70° to 120° C. Higher temperatures, e.g., 250° to 450° C., can be employed for a gas phase reaction if necessary. Elevated pressures can be used if desired, but for ease of operation, operation at ambient pressure is employed or, alternatively, at a pressure modestly in excess of ambient, e.g., sufficient to cause the reactants and products to pass through a reactor in a continuous process.

If the reaction is conducted in a batchwise manner, it can be run in a stirred reactor vessel into which the materials are charged. If the reaction is conducted continuously, it can be run in a continuous stirred tank reactor or, preferably, in a continuous plug flow process, e.g., in a tubular reactor. In a stirred reactor, the catalyst will normally reside within the reactor vessel. At the conclusion of a batchwise process, the catalyst will be removed from the products by suitable means, such as decantation, filtration, or centrifugation. In a continuous tank process, the catalyst will be retained in the reactor by other means which will be apparent to those skilled in the art of reactor design. In a continuous tubular reactor, the catalyst will normally be present as a fixed bed.

The amount of the catalyst employed will typically be 0.1 to 50 percent by weight, based on the weight of the nitrile charged, and preferably 1 to 20 percent. These amounts are particularly directed to the reaction when it is conducted batchwise. When the reaction is run continuously, the amount of catalyst is better expressed in terms of liquid hourly space velocity, which is the mass of product obtained from the reactor per hour, per unit mass of catalyst employed. Continuous reactions as contemplated by the present invention typically exhibit a liquid hourly space velocity of 0.01 to 100, preferably 0.1 to 10, depending on temperature and other variables.

In the present process the catalyst can be replaced after every batch, but it is more economical to reuse the catalyst for multiple batches, or to run a continuous process for a relatively long period of time using the same catalyst. After extended use, however, the activity of the catalyst may diminish. An advantage of the present catalyst system is that the catalyst can be reactivated, or regenerated, by heating under air or oxygen flow. Typically heat treatment of the clay will be at 150° to 450° C. As a part of the reactivation procedure, the clay can be reacidified by treatment with acid.

The particular conditions of time, temperature, pressure, and catalyst amount for a specific reaction will need to be determined according to the activity of the reactants. Such adjustments can be readily made by the person skilled in the art. Thus if little or no reaction occurs at a relatively low temperature, or at a relatively low pressure, or using a short reaction time, the conditions can be adjusted by increasing the temperature or reaction time or pressure or by adjusting the catalyst concentration.

PRODUCT: HYDROCARBYL-SUBSTITUTED AMIDE

The present reaction will lead to hydrocarbylation on the nitrogen atom of the nitrile, depending on the specific reaction conditions and the nature of the specific nitrile reactant.

The present invention permits N-hydrocarbyl-substituted amides to be prepared more efficiently without the use of conventional acidic materials such as $AlCl_3$ or sulfuric acid, which cause environmental or handling difficulties, are corrosive, and are not generally reusable. The N-hydrocarbyl-substituted amide products prepared by the present process include such materials as tert-octyl acrylamide, a monomer used in associative thickeners, hair spray resins, and shampoos; and iso-propyl acrylamide, which displays a lower critical solution temperature in homopolymer form and is useful in controlled drug delivery and thermally-activated gel applications. In a preferred case the product will be t-butyl acrylamide, useful in hair care products, adhesives, water treatment polymers, and oil field polymers.

The N-hydrocarbyl-substituted amide products prepared by the present process also include such materials as 1-chloro-tert-amyl acrylamide, a substance with broad application to cationic resin, paper, oil field, water treatment, and person care uses; diacetone acrylamide, which is useful in applications ranging from emulsion polymerization to coatings (as methylol derivative) to contact lenses; isopropylidene bisacrylamide, a material used as a cross-linking agent, in non-wovens, and in superabsorbent applications; butenyl acrylamide, a substance with application to graphic arts coatings and photo-curable resins; and acrylamidomethylbutryate, which has applications in connection with pH-sensitive polymers.

EXAMPLES

Example 1

To a 50 mL reaction tube containing a magnetic stir bar is charged 2.32 g Superfiltrol® acidified clay, 38.7 g acrylonitrile, and 5.61 g t-butanol. The tube is sealed with a threaded Teflon™ stopper and a silicone rubber o-ring and is immersed, up to the depth of the liquid, in an oil bath heated to 72° C. The reaction mixture is stirred at temperature for 12 hours.

Upon cooling to room temperature, the tube is subjected to centrifugation for 1 hour, leading to separation of the solids. The supernatant liquid is decanted and reduced to constant weight on a rotary evaporator to isolate 0.96 g product.

Examples 2–5

The solid catalyst recovered at the bottom of the reaction tube in Example 1 is immediately charged with fresh acrylonitrile and t-butanol, and the reaction mixture is treated as in Example 1. The yield of adduct after repeated reuses of the catalyst is shown in the following table:

| Example | Catalyst | t-Butanol charged, g | Yield: g |
| --- | --- | --- | --- |
| 1 | first use | 5.61 | 0.96 |
| 2 | second use | 5.61 | 1.02 |
| 3 | third use | 3.63 | 0.33 |
| 4 | fourth use | 3.60 | 0.43 |
| 5 | fifth use[a] | 2.09 | 0.30 |

[a]clay heated to 425° C. in air prior to reuse.

In the table, the amount of catalyst employed is reduced after the second and fourth uses. The amount of butanol charged is correspondingly reduced, and the absolute yield of product, in grams, is similarly reduced. However, the percent yield of product shows less variation.

Example 6

To a 100 mL Parr bomb is charged 61.11 g of a mixture of acrylonitrile/t-butanol in a 10:1 molar ratio, along with 3.23 g Superfiltrol™. The bomb is sealed with ambient pressure air in the headspace, and the mixture heated to 120° C. with maximum stirring. The pressure in the bomb reaches 520 kPa (75 psig). The reaction is maintained at temperature for 12 hours. Upon cooling, the contents are poured into a bottle and centrifuged to remove the solids. The liquid is dried to constant weight on a rotary evaporator to obtain 3.79 g white solids.

Examples 7–9

Example 1 is substantially repeated, using a glass reaction flask, a 10:1 molar mixture of acrylonitrile and t-butanol, and Superfiltrol™ acidified clay catalyst in the amounts indicated in the following table:

| Example | Catalyst | t-Butanol, g | Yield, g |
|---------|----------|--------------|----------|
| 7 | first use | 3.30 | 0.62 |
| 8 | second use | 3.30 | 1.05 |
| 9 | third use | 3.29 | 0.88 |

Example 10

To a reaction flask equipped with a magentic stirrer is charged 66.45 g acrylonitrile, 9.30 g t-butanol, and 3.98 g F-24 acidified clay (Englehard). The mixture is heated to 72° C. for 12 hours. Upon cooling, the mixture is filtered through filter paper. The resulting solids are washed with a 1:1 mixture by volume of toluene and methanol and filtered again. The organic liquids are combined and evaporated to constant weight to provide 3.07 g of white solid product.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. As used herein, the expression "consisting essentially of" permits the inclusion of substances which do not materially affect the basic and novel characteristics of the composition under consideration.

What is claimed is:

1. A process for the preparation of a hydrocarbyl-substituted amide via the Ritter reaction using a solid clay catalyst, comprising contacting:
   (a) a nitrile with
   (b) a hydrocarbylating agent, in the presence of
   (c) a solid catalyst comprising an acidified clay under conditions conducive to the formation of the hydrocarbyl-substituted amide, wherein said catalyst retains catalytic activity over the course of several Ritter reactions and wherein said process does not generate aqueous sulfate waste.

2. The process of claim 1 wherein the nitrile is unsaturated.

3. The process of claim 1 wherein the nitrile is saturated.

4. The process of claim 2 wherein the nitrile is acrylonitrile.

5. The process of claim 3 wherein the nitrile is butyronitrile.

6. The process of claim 1 wherein a condition conducive to the formation of the hydrocarbyl-substituted amide comprises contacting at least one mole of water per mole of component (b) with components (a), (b), and (c).

7. The process of claim 1 wherein the hydrocarbylating agent comprises an olefin.

8. The process of claim 7 wherein the olefin is a branched-chain olefin.

9. The process of claim 7 wherein the olefin contains an average of 2 to about 200 carbon atoms.

10. The process of claim 7 wherein the olefin is propylene.

11. The process of claim 8 wherein the branched-chain olefin is 2-methyl-1-propene.

12. The process of claim 8 wherein the branched-chain olefin is a trimethylpentene.

13. The process of claim 1 wherein the hydrocarbylating agent is an alcohol.

14. The process of claim 13 wherein the alcohol is a secondary alcohol.

15. The process of claim 13 wherein the alcohol is a tertiary alcohol.

16. The process of claim 14 wherein the secondary alcohol is 2-propanol.

17. The process of claim 15 wherein the tertiary alcohol is 2-methyl-2-propanol.

18. The process of claim 1 wherein the hydrocarbylating agent is substituted with at least one non-hydrocarbon group.

19. The process of claim 18 wherein the hydrocarbylating agent is substituted at least one alkoxy group.

20. The process of claim 19 wherein the hydrocarbylating agent is a mixture of alkoxylated alcohols.

21. The process of claim 1 wherein the clay is present in an amount of about 2 percent to about 20 percent by weight of the reaction mixture.

22. The process of claim 1 wherein the clay is an acidified montmorillonite clay.

23. The process of claim 1 wherein the clay is acidified with a Lewis acid or a Brønsted acid.

24. The process of claim 1 wherein the clay contains about 0.1 to about 1.0 equivalent acid per gram of clay.

25. The process of claim 1 wherein the clay is recovered after the amide-forming reaction and is used in a subsequent amide-forming reaction.

26. The process of claim 25 wherein the recovered clay is reacidified by treatment acid.

27. The process of claim 25 wherein the recovered clay is subjected to heat treatment prior to use in the subsequent reaction.

28. The process of claim 25 wherein the heat treatment is conducted at about 150° about 450° C.

29. The process of claim 1 wherein the process is conducted at an average temperature of about 50° C. to about 150° C.

30. The process of claim 1 wherein the process is conducted at an average temperature of about 70° C. to about 120° C.

31. The process of claim 1 wherein the process is conducted at an average pressure of about 1 atmosphere to about 20 atmospheres.

32. The process of claim 1 wherein the process is a continuous process.

33. The process of claim 32 wherein the process is conducted in a continuous stirred tank reactor.

34. The process of claim 32 wherein the process is a continuous plug flow process.

35. The process of claim 32 wherein the process is conducted in a tubular reactor.

36. The process of claim 32 wherein the process has an average liquid hourly space velocity of about 0.1 to about 10.

37. The product prepared by the process of claim 1.

* * * * *